United States Patent [19]

Speakman et al.

[11] Patent Number: 5,084,272
[45] Date of Patent: Jan. 28, 1992

[54] TRICHODERMA FUNGUS AND FUNGICIDE CONTAINING IT

[75] Inventors: John-Bryan Speakman, Mannheim; Maria Scherer, Godramstein; Heidrun Anke, Kaiserslautern, all of Fed. Rep. of Germany

[73] Assignee: BASF Aktiengesellschaft, Ludwigshafen, Fed. Rep. of Germany

[21] Appl. No.: 480,761

[22] Filed: Feb. 16, 1990

[30] Foreign Application Priority Data

Feb. 16, 1989 [DE] Fed. Rep. of Germany ....... 3904710

[51] Int. Cl.$^5$ .................. C12N 1/14; A01N 63/04
[52] U.S. Cl. .................................. 424/93; 435/254
[58] Field of Search ........................ 435/254; 424/93

[56] References Cited

U.S. PATENT DOCUMENTS 4,713,342  12/1987  Chet et al. .......................... 435/254

OTHER PUBLICATIONS

*ATCC Catalogue of Fungi Yeasts*, 17th Edition, 1987.

*Primary Examiner*—Douglas W. Robinson
*Assistant Examiner*—Marian C. Knode
*Attorney, Agent, or Firm*—Oblon, Spivak, McClelland, Maier & Neustadt

[57] ABSTRACT

A fungus Trichoderma sp-34/84, and fungicides containing the same which are used in controlling Pythium fungi.

8 Claims, No Drawings

TRICHODERMA FUNGUS AND FUNGICIDE CONTAINING IT

BACKGROUND OF THE INVENTION

1. Field of the Invention

The present invention relates to the fungus Trichoderma sp.-35/84, a fungicide which contains it and a method for controlling pythium rot, wherein the fungus Trichoderma sp.-35/84 is applied to the seeds of the plant or to the soil.

2. Description of the Background

It is known that, during germination and emergence, plants and their seedlings may be attacked and damaged by fungi which occur in the soil (soil-borne fungi). An important group of phytopathogenic soil fungi comprises the Pythium fungi, which cause pythium rot.

Where this fungal disease is present, the bases of the stems of seedlings become soft and collapse, or the fungus penetrates via the roots into the vascular strands of the plant and blocks them, causing the plant to wilt. The result may then be considerable losses of plants and reduced yields.

SUMMARY OF THE INVENTION

We have found that the fungus Trichoderma sp.-35/84 can advantageously be used for controlling fungi, in particular soil-borne fungi, especially Pythium fungi.

DESCRIPTION OF THE PREFERRED EMBODIMENTS

Trichoderma sp.-35/84 is a naturally occurring fungal species. It has been deposited under number IMI 311 756 at the C.A.B. International Mycological Institute, Kew, England, and under the number DSM 5067 at the Deutsche Sammlung von Mikroorganismen und Zellkulturen, Brunswick, West Germany.

The present invention relates, inter alia, to a method for controlling pythium rot in various plant species, wherein the fungal species Trichoderma sp.-35/84 is applied to the seeds or mixed with the soil. Trichoderma sp.-35/84 is not pathogenic to humans or animals and is not a phytopathogenic fungus.

Soil-borne fungi are, for example, Pythium fungi. The fungus Trichoderma is used in a fungicidal amount, for example at an application rate of from $10^6$ to $10^{10}$ colony-forming units per ml of spore suspension. Colony-forming units are both the spores and mycelium fragments. The fungus Trichoderma sp.-35/84 is understood as meaning both its mycelium and its spores. The fungicidal action of Trichoderma sp.-35/84 is particularly well displayed in plants which are susceptible to pythium rot, for example the leguminosae (peas and beans), the cruciferae (rape and radish) and the solanaceae (tomatoes and potatoes).

The fungal species to be used according to the invention can be grown by culturing on suitable substrates, such as grain, straw or other plant materials, or with the aid of conventional solid culture media, such as potato dextrose agar, malt agar or yeast extract agar, if necessary on suitable substrates, such as cornflour/sand mixtures or plastics, or on appropriate liquid culture media without the addition of agar.

The present invention also relates to crop protection agents which contain Trichoderma sp.-35/84 as mycelia and/or spores, in addition to suitable diluents, such as water, and/or assistants. The assistants used may be conventional additives, such as adhesives or emulsifiers.

The fungus can be used in the form of colony-forming units, for example as mycelia or in the form of spores (conidia or chlamydospores) or mycelium fragments or mycelium conglomerates.

The novel agents can be used in the form of wettable powders, emulsifiable concentrates, atomizable solutions (dispersions), dusting agents, dressings, dispersions, granules or microgranules in the usual formulations.

The commercial concentrates are used by diluting them in a conventional manner if necessary, for example in the case of wettable powders, emulsifiable concentrates, dispersions and water-dispersible (micro)granules with water. Dust-like, granulated and dressing formulations are usually not diluted with further inert substances before being used. Mixtures or mixed formulations with other fungicides or nonfungicidal active ingredients, such as insecticides, acaricides, herbicides, fertilizers or growth regulators, are also possible, and in some cases it is also possible to increase the activity in a synergistic manner.

The Examples which follow illustrate the invention.

Biological Examples

A) Preparation of the Inoculum a) Glass dishes which contained 2% strength malt extract agar (MEA) were inoculated with spores or mycelia of Trichoderma sp.-35/84. The inoculated agar was incubated for from 8 to 21 days at from 23° to 25° C. with or without black light (NUV). Water was then used to obtain a spore suspension, which is diluted to $10^6$–$10^{10}$, in particular $10^8$, spores/ml.

b) As described in a), an aqueous spore suspension of Trichoderma sp.-35/84 was prepared. Inoculation was then effected with the freshly produced spore suspension in 500 ml glass flasks which had already been filled with sterilized, moist swollen oat grains. After about 14 days, when the grains were overgrown with the fungus and the spores had formed, the fungus-covered grains were shaken with water, and the spore suspension thus obtained was diluted to $10^6$–$10^{10}$, in particular $10^8$, spores/ml.

B) Greenhouse Experiments

EXAMPLE B1

A Pythium ultimum isolate which had been isolated from naturally infested pea plants was cultured on 2% strength MEA. Sterilized, moist cornflour/quartz sand mixtures or soil were then inoculated with Pythium ultimum mycelium/agar pieces from this culture in 500 ml glass flasks. After about 14 days, when the Pythium fungus had grown throughout the medium, the latter was used to infest doubly steam-sterilized soil with the pathogen, in a mixing ratio of 1 g of fungal inoculum per 1 kg of steam-sterilized soil. 500 g of infested soil were then taken and a 14 day old agar culture of the fungus Trichoderma sp.-35/84 was mixed in. This treated soil was placed in plastic pots. The prepared pots were each sown with 10 pea seeds and placed in a greenhouse chamber at 20° C. The steam-sterilized soil served as the untreated control, the soil mixed with the cornflour/quartz sand served as the infested control and a soil sample which was not infested but had been treated with Trichoderma sp.-35/84 was used as a phytotoxicity control. The experiment was repeated on three different dates. For comparison, a *Trichoderma harzianum* strain was used instead of *Trichoderma sp.-35/84*. The results are shown in the Table below.

TABLE 1

| Treatment | Number of healthy plants in 2 pots | | | Efficiency % | | |
|---|---|---|---|---|---|---|
| | I | II | III | I | II | III |
| Treated | 20 | 20 | 20 | — | — | — |
| Infested | 0 | 0 | 0 | — | — | — |
| Infested + Trichoderma sp-35/84 | 10 | 10 | 7 | 50 | 50 | 35 |
| Infested + Trichoderma harzianum | 6 | 6 | 5 | 30 | 30 | |
| Trichoderma sp-35/84 | 20 | 20 | 20 | — | — | — |
| Trichoderma harzianum | 20 | 20 | 20 | — | — | — |

EXAMPLE B2

Experiments were carried out using the same *Pythium ultimum* isolate as in B1, the peas being treated with an aqueous *Trichoderma sp.-35/84* spore suspension which had been obtained according to Method Aa). The seeds were immersed in the suspension for 24 hours and then sown in the soil samples infested in various ways. The experiment was likewise carried out at 20° C. in a greenhouse and repeated on three different dates. The comparison with the *Trichoderma harzianum* strain was also carried out. The results are shown in the Table below.

TABLE 2

| Treatment | Number of healthy plants in 2 pots | | | Efficiency % | | |
|---|---|---|---|---|---|---|
| | I | II | III | I | II | III |
| Treated | 20 | 20 | 20 | — | — | — |
| Infested | 0 | 1 | 3 | — | — | — |
| Infested + Trichoderma sp-35/84 | 16 | 17 | 12 | 80 | 85 | 60 |
| Infested + Trichoderma harzianum | 7 | 12 | 6 | 35 | 60 | 30 |
| Trichoderma sp-35/84 | 20 | 20 | 20 | — | — | — |
| Trichoderma harzianum | 20 | 20 | 20 | — | — | — |

C) Field Trials

EXAMPLE

Pea seeds which had been treated by the method described under B2 were sown on an area where preliminary tests had shown that there was natural Pythium infestation. The results below were obtained in three independent trials.

TABLE 3

| | Result after ... days | % attack in the | | Efficiency of the treatment in % |
|---|---|---|---|---|
| | | untreated control | treated sample | |
| Trial 1 | 26 | 47.3 | 22.0 | 53.5 |
| Trial 2 | 30 | 68.8 | 30.0 | 56.4 |
| Trial 3 | 35 | 89.6 | 11.7 | 86.3 |

As shown by the values in the Table above, damage to the pea plants is substantially reduced when *Trichoderma sp.-35/84* is used.

We claim:

1. A biologically pure culture of fungus *Trichoderma sp.* 35/84.

2. A fungicide comprising a fungicidally effective amount of the fungus *Trichoderma sp.* 35/84 and a carrier.

3. A method of controlling Pythium rot in plants which are susceptible thereto, which comprises applying a fungicidally effective amount of *Trichoderma sp.* 35/84 onto the seeds of said plants or mixing a fungicidally effective amount of *Trichoderma sp.* 35/84 with soil in proximity to said plants or both.

4. The method as claimed in claim 3, wherein said plants susceptible to Pythium rot are selected from the group consisting of leguminosae, cruciferae and solanaceae plants.

5. A method for controlling Pythium fungi which comprises applying a fungicidally effective amount of the fungus *Trichoderma sp.* 35/84 on the fungi, or on seeds or soil.

6. The method according to claim 5, wherein soil-borne Pythium fungi are controlled.

7. The method of claim 5, wherein *Trichoderma sp.* 35/84 is applied in an amount of from about $10^6$ to $10^6$ colony-forming units per ml. of spore suspension.

8. The method of claim 5, wherein a fungicidally effective amount of *Trichoderma sp.* 35/84 is applied to seeds of plants susceptible to Pythium.

* * * * *